United States Patent
Sato et al.

(10) Patent No.: US 7,174,854 B2
(45) Date of Patent: Feb. 13, 2007

(54) BODY TEMPERATURE HOLDING DEVICE WITH HEART RATE AND RESPIRATION RATE DETECTING FUNCTION FOR SMALL ANIMALS AND HEART RATE AND RESPIRATION RATE MEASURING SYSTEM FOR SMALL ANIMALS USING THE DEVICE

(75) Inventors: Shinichi Sato, Akita (JP); Katsuya Yamada, Akita (JP); Nobuya Inagaki, Akita (JP)

(73) Assignee: Japan Science and Technology Agency, Kawaguchi (JP)

( * ) Notice: Subject to any disclaimer, the term of this patent is extended or adjusted under 35 U.S.C. 154(b) by 140 days.

(21) Appl. No.: 10/503,985

(22) PCT Filed: Feb. 4, 2003

(86) PCT No.: PCT/JP03/01109

§ 371 (c)(1),
(2), (4) Date: Aug. 10, 2004

(87) PCT Pub. No.: WO03/067967

PCT Pub. Date: Aug. 21, 2003

(65) Prior Publication Data

US 2005/0039699 A1    Feb. 24, 2005

(30) Foreign Application Priority Data

Feb. 14, 2002 (JP) .............................. 2002-036620

(51) Int. Cl.
*A01K 29/00* (2006.01)

(52) U.S. Cl. ...................................... 119/712; 119/412
(58) Field of Classification Search ................ 119/712, 119/28.5, 174, 421, 850, 859
See application file for complete search history.

(56) References Cited

U.S. PATENT DOCUMENTS

| | | | | | |
|---|---|---|---|---|---|
| 3,136,577 | A | * | 6/1964 | Richard | 297/180.11 |
| 4,438,771 | A | * | 3/1984 | Friesen et al. | 600/484 |
| 4,862,144 | A | * | 8/1989 | Tao | 340/573.1 |
| 4,930,317 | A | * | 6/1990 | Klein | 62/3.3 |
| 5,515,865 | A | * | 5/1996 | Scanlon | 600/534 |
| 5,871,526 | A | * | 2/1999 | Gibbs et al. | 607/104 |
| 5,948,303 | A | * | 9/1999 | Larson | 219/486 |
| 6,485,506 | B2 | * | 11/2002 | Augustine | 607/96 |

FOREIGN PATENT DOCUMENTS

| | | |
|---|---|---|
| JP | 59-122949 | 7/1984 |
| JP | 10-108578 | 4/1998 |
| JP | 11-18602 | 1/1999 |
| JP | 2002-51662 | 2/2002 |
| JP | 2002-250532 | 9/2002 |

* cited by examiner

Primary Examiner—Son T. Nguyen
(74) Attorney, Agent, or Firm—Bacon & Thomas, PLLC

(57) ABSTRACT

A device, for maintaining body temperature with detection of heart rate and respiratory rate small animals, has a layered structure and includes a sheet-like pressure-sensitive sensor superimposed on a flat-plate heater and sandwiched between thin insulation sheets. A spacer formed of a metallic plate, having a hole into which the pressure-sensitive sensor is fitted, is also provided between the thin insulation sheets.

11 Claims, 8 Drawing Sheets

(a)

(b)

BODY TEMPERATURE HOLDING DEVICE WITH HEART RATE AND RESPIRATION RATE DETECTING FUNCTION FOR SMALL ANIMALS AND HEART RATE AND RESPIRATION RATE MEASURING SYSTEM FOR SMALL ANIMALS USING THE DEVICE

CROSS-REFERENCE TO RELATED APPLICATIONS

This application is a National Phase Application (35 USC 371) of PCT/JP03/01109 and claims priority of Japanese Application No. 2002-36620, filed Feb. 14, 2002.

TECHNICAL FIELD

The present invention relates to a device for maintaining body temperature having heart rate and respiratory rate detection function for small animals and to a heart rate and respiratory rate measurement system for small animals using the device.

BACKGROUND ART

The inventors of the present invention have already proposed a heater device for keeping a mouse whose body temperature is decreased due to anesthesia in a normal physiological state in "body temperature keeping device for small animal", particularly for a mouse (Japanese Unexamined Patent Application Publication No. 2002-51662). The respiratory rate and heart rate of a small animal are not subject to measurement in this heater device.

However, monitoring the respiratory rate and heart rate of an anesthetized animal, in addition to maintaining the body temperature of the animal, in a physiological experiment is essential for determining the physiological state of the animal.

Although there are known technologies for measuring the body temperature or respiratory rate of human beings to keep them in a comfortable state on a carpet used by the human beings, it is necessary to devise measuring methods specific to small animals in order to measure the physiological state of the animals that are much smaller than human beings. Simple and reliable physiological and experimental devices for small animals have not yet been provided.

DISCLOSURE OF THE INVENTION

As described above, electrodes for electrocardiograms or respiratory monitoring devices suitable for very small animals, such as mice, have hardly been available. Although electrodes for electrocardiograms or the like handmade by researchers have been used in experiments in the present circumstances, they can cause an animal pain because they are not optimum. In addition, there are numerous cases in which it is quite difficult to mount the electrodes for the electrocardiogram or the like. Accordingly, it disadvantageously takes a long time to prepare for monitoring the respiratory rate and heart rate of a small animal.

In order to solve the problems described above, it is an object of the present invention to provide a device for maintaining body temperature having heart rate and respiratory rate detection function for small animals and a heart rate and respiratory rate measurement system for small animals using the device, which are capable of being simply and easily set up without causing the small animal pain.

[1] A device for maintaining body temperature having heart rate and respiratory rate detection function for small animals includes a flat-plate heater; a pressure-sensitive sensor that is sandwiched between thin insulation sheets provided over the flat-plate heater; a spacer provided between the thin insulation sheets; and a temperature sensor provided on the spacer.

[2] In the device for maintaining body temperature having heart rate and respiratory rate detection function for small animals described in [1], the spacer is characterized by being a metallic plate having a hole into which the pressure-sensitive sensor fits.

[3] A heart rate and respiratory rate measurement system for small animals includes a flat-plate heater; a pressure-sensitive sensor that is sandwiched between thin insulation sheets provided over the flat-plate heater; a spacer provided between the thin insulation sheets; a temperature sensor provided on the spacer; a control device for maintaining the body temperature of each of the small animals and for acquiring information from the pressure-sensitive sensor to determine respiratory rate and heart rate in a state where the chest of the small animal is placed on the pressure-sensitive sensor; and a monitoring device for monitoring the respiratory rate and heart rate of the small animal.

[4] In the heart rate and respiratory rate measurement system for small animals described in [3], the spacer is characterized by being a metallic plate having a hole into which the pressure-sensitive sensor fits.

[5] The heart rate and respiratory rate measurement system for small animals described in [4] is characterized by further including a low band-pass filter for processing the information acquired from the pressure-sensitive sensor to measure the respiratory rate of each of the small animals and a high band-pass filter for measuring the heart rate of the small animal.

[6] The heart rate and respiratory rate measurement system for small animals described in [4] is characterized by providing a terminal through which analog output waveforms of heartbeats and respiration are output after an electrical signal is filtered through the filters, and characterized by converting the electrical signal into a digital signal based on the output from the terminal to measure the heart rate and the respiratory rate.

[7] The heart rate and respiratory rate measurement system for small animals described in [4] is characterized by providing a terminal through which analog output waveforms of heartbeats and respiration are output after an electrical signal is filtered through the filters, and characterized by including an observation device for observing the heartbeats and the respiration based on the output from the terminal.

[8] The heart rate and respiratory rate measurement system for small animals described in [6] is characterized by having a microprocessor including a storage medium that stores a program for eliminating pulses caused by noise among the digitized heartbeat pulses and for determining whether a pattern is such that one pulse corresponds to one heartbeat or a pattern is such that two pulses correspond to one heartbeat.

[9] The heart rate and respiratory rate measurement system for small animals described in [6] is characterized by supplying a signal obtained by filtering the output from the pressure-sensitive sensor through a high-pass filter and amplifying the filtered output and an output from an integration circuit that receives the amplified signal to a differential amplifier to configure a high band-pass filter circuit that supplies the output from the differential amplifier as the analog signal waveforms.

[10] The heart rate and respiratory rate measurement system for small animals described in [6] is characterized by configuring a circuit for generating the digital signal for measuring the heart rate by connecting a circuit, in which a positive-signal peak-hold circuit and a negative-signal peak-hold circuit, which have a holding time of around several milliseconds, are connected to the two input terminals of the differential amplifier, to an output terminal of the high band-pass filter circuit described in [9].

[11] The heart rate and respiratory rate measurement system for small animals described in [10] is characterized in that each of the peak-hold circuits has a capacitor connected in parallel to a resistor in a rectification circuit having a diode connected in series to the resistor.

As described above, according to the present invention, the sheet pressure-sensitive sensor is provided on an area on the surface of the heater. The area is covered with the chest of a small animal (the portion beneath the heart) when the small animal is placed on the heater for maintaining the body temperature thereof. It is possible to detect the oscillation (change in pressure) due to the respiration and heartbeats of the small animal that is in contact with the pressure-sensitive sensor to monitor the respiratory rate and the heart rate of the small animal.

In other words, the device for detecting the respiratory rate and heart rate is integrated on the surface of the heater for maintaining the body temperature, so that not only the body temperature of the small animal can be maintained but also the respiratory rate and heart rate of the small animal can be monitored.

BEST MODE FOR CARRYING OUT THE INVENTION

Embodiments of the present invention will be described in detail below.

Figure 1:
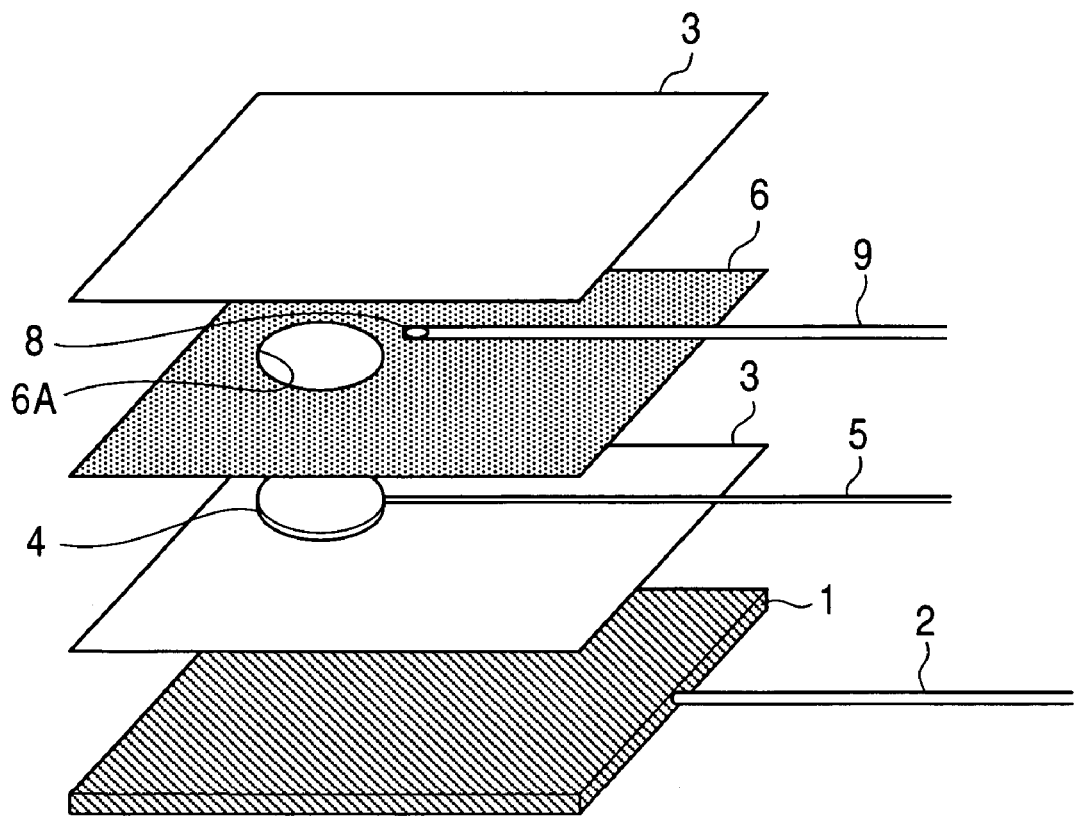
FIG. 1 includes diagrams showing the structure of a device for maintaining body temperature having heart rate and respiratory rate detection function for small animals according to an embodiment of the present invention.
Figure 1:
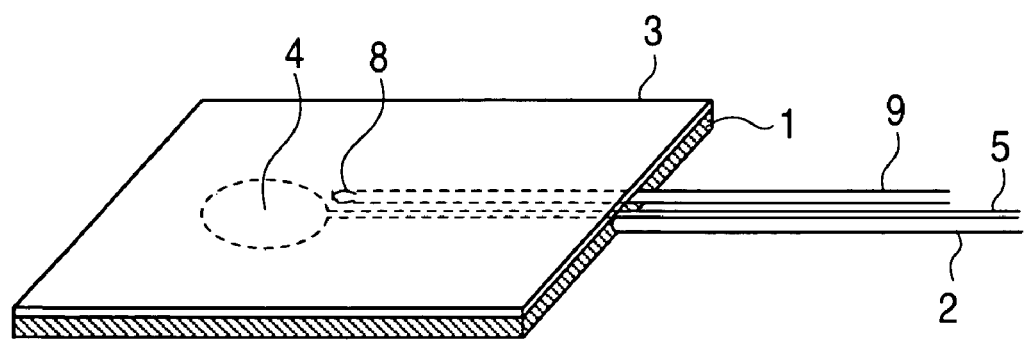
Figure 2:
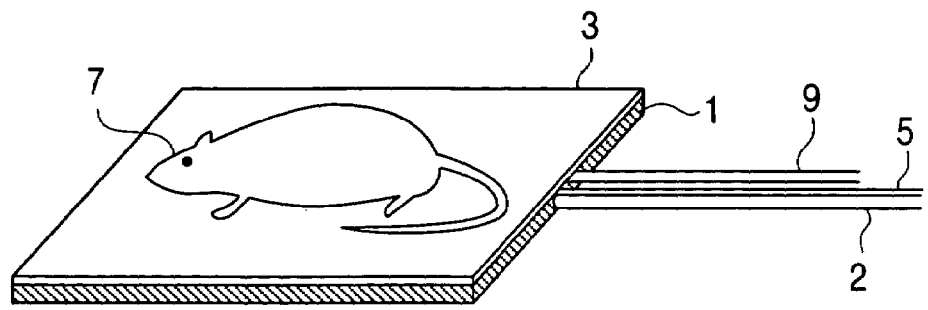
FIG. 2 illustrates a state in which a mouse is placed on the device for maintaining body temperature having heart rate and respiratory rate detection function for small animals according to the embodiment of the present invention.
Figure 3:
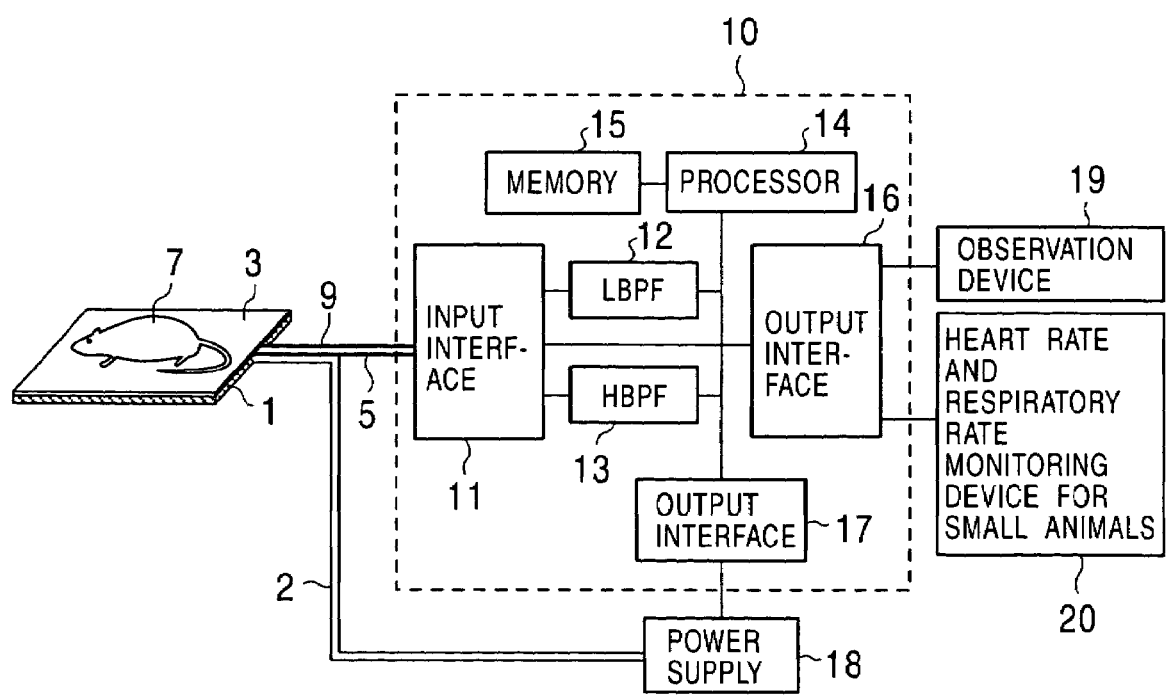
FIG. 3 is a block diagram of a heart rate and respiratory rate measurement system for small animals using the device for maintaining body temperature having heart rate and respiratory rate detection function for small animals, according to an embodiment of the present invention.

FIG. 1 includes diagrams showing the structure of a device for maintaining body temperature having heart rate and respiratory rate detection function for small animals according to an embodiment of the present invention. FIG. 1(a) is an exploded perspective view of the device for maintaining body temperature having heart rate and respiratory rate detection function for small animals. FIG. 1(b) is a perspective view of the device for maintaining body temperature having heart rate and respiratory rate detection function for small animals. FIG. 2 illustrates a state in which a mouse is placed on the device for maintaining body temperature having heart rate and respiratory rate detection function for small animals. FIG. 3 is a block diagram of a heart rate and respiratory rate measurement system for small animals using the device for maintaining body temperature having heart rate and respiratory rate detection function for small animals.

Referring to FIGS. 1(a) to 3, reference numeral 1 denotes a flat-plate heater, reference numeral 2 denotes a heater-current supplying line, reference numeral 3 denotes a thin insulation sheet, reference numeral 4 denotes a sheet pressure-sensitive sensor, reference numeral 5 denotes a signal line of the pressure-sensitive sensor 4, reference numeral 6 denotes a spacer, reference numeral 6A denotes a hole formed in the spacer 6, into which the pressure-sensitive sensor 4 fits, reference numeral 7 denotes a mouse, reference numeral 8 denotes a temperature sensor, reference numeral 9 denotes a signal line of the temperature sensor 8, reference numeral 10 denotes a control device, reference numeral 11 denotes an input interface, reference numeral 12 denotes a low band-pass filter (LBPF), reference numeral 13 denotes a high band-pass filter (HBPF), reference numeral 14 denotes a processor, reference numeral 15 denotes a storage unit (memory: storage medium) for storing programs, reference numerals 16 and 17 denote output interfaces, reference numeral 18 denotes a power supply, reference numeral 19 denotes an observation device, and reference numeral 20 denotes a heart rate and respiratory rate monitoring device for small animals.

As shown in FIG. 1(a), the sheet pressure-sensitive sensor 4 (piezoelectric device or the like), which is sandwiched between the thin insulation sheets 3, 3 or the like, is disposed over the flat-plate heater 1 to which the heater-current supplying line 2 is connected.

The hole 6A into which the pressure-sensitive sensor 4 fits is formed in the spacer 6. The spacer 6 is preferably a metallic plate in order to equalize the temperature distribution and to disperse the load of a small animal.

The signal line 5 of the pressure-sensitive sensor 4 and the signal line 9 of the temperature sensor 8 are connected to the control device 10. The heater-current supplying line 2 is connected to the power supply 18, which can be controlled by the control device 10.

Since the output from the pressure-sensitive sensor 4 is an electrical signal on which the respiratory rate and heart rate of a small animal (for example, the mouse 7 in FIG. 2) are superimposed, filtering the electrical signal through the low band-pass filter (LBPF) 12 produces a waveform corresponding to the respiration of the small animal and filtering the electrical signal through the high band-pass filter (HBPF) 13 produces a waveform corresponding to the heartbeat of the small animal. In other words, a process for separating, shaping and displaying the electrical signal, on which the respiratory rate and the heart rate output from the pressure-sensitive sensor 4 are superimposed, is performed. The shaped signal is observed on the external observation device (for example, an oscilloscope) 19. Furthermore, the frequency of the signal is measured and the measured frequency is displayed on an LED screen to monitor the respiratory rate and the heart rate of the small animal with the monitoring device 20. The body temperature of the small animal, which is output from the temperature sensor 8, can be controlled by the control device 10. Detection means of heartbeat signals according to the present invention will now be described in detail.

Figure 4:
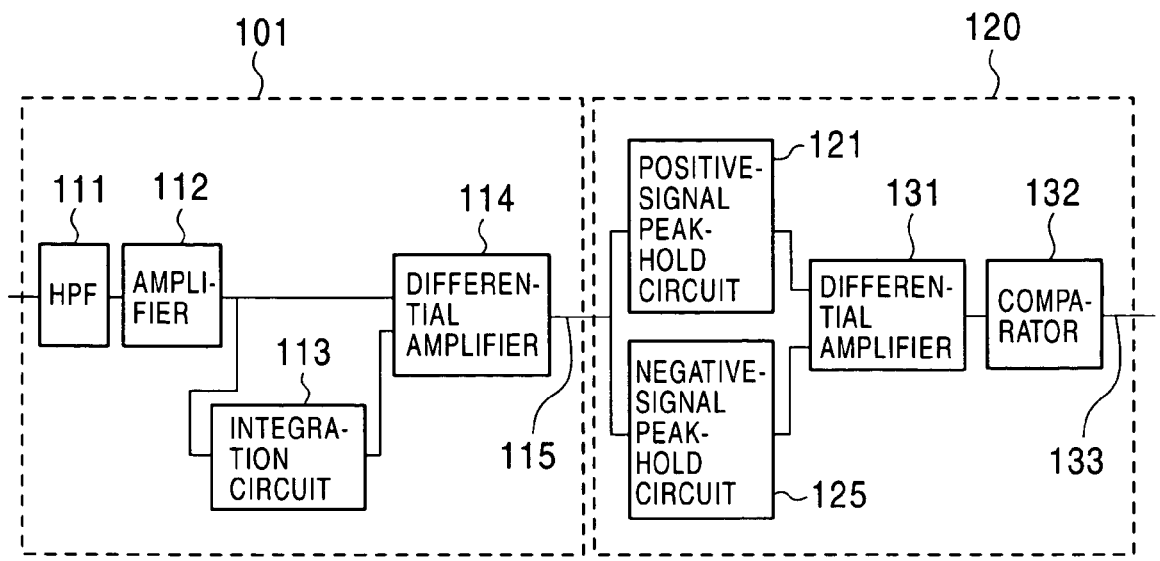
FIG. 4 shows an exemplary circuit for detecting a heartbeat signal used in the device for maintaining body temperature having heart rate and respiratory rate detection function for small animals according to an embodiment of the present invention.
Figure 5:
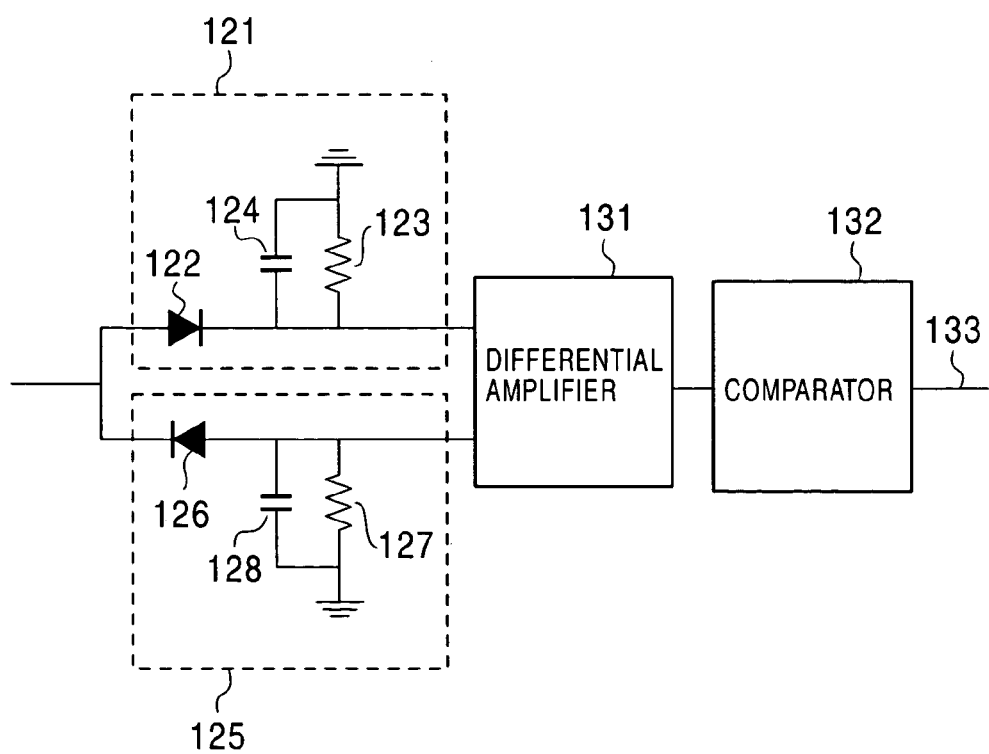
FIG. 5 is a circuit diagram of a heartbeat-signal shaping circuit, which is a simple circuit example that specifically realizes a peak-hold circuit, used in the device for maintaining body temperature having heart rate and respiratory rate detection function for small animals according to an embodiment of the present invention.

FIG. 4 shows an exemplary circuit for detecting a heartbeat signal, used in the device for maintaining body temperature having heart rate and respiratory rate detection function for small animals, according to an embodiment of the present invention. FIG. 5 is a circuit diagram of a heartbeat-signal shaping circuit, which is a simple circuit example that specifically realizes a peak-hold circuit, used in the device for maintaining body temperature having heart rate and respiratory rate detection function for small animals.

Referring to FIGS. 4 and 5, reference numeral 101 denotes a high band-pass filter circuit (HBPF) including an HPF (high-pass filter) 111, an amplifier 112, an integration circuit 113, and a differential amplifier 114. Reference numeral 115 denotes an output signal line of the differential amplifier 114.

Reference numeral 120 denotes a heartbeat-signal shaping circuit. Reference numeral 121 denotes a positive-signal peak-hold circuit including a diode (forward connection) 122, and a resistor 123 and a capacitor 124 connected in parallel between the output side of the diode 122 and the ground. Reference numeral 125 denotes a negative-signal peak-hold circuit including a diode 126 (backward connection), and a resistor 127 and a capacitor 128 connected in parallel between the output side of the diode 126 and the ground. Reference numeral 131 denotes a differential amplifier to which the output signal from the positive-signal peak-hold circuit 121 and the output signal from the negative-signal peak-hold circuit 125 are supplied, reference numeral 132 denotes a comparator connected to the differential amplifier 131, and reference numeral 133 denotes an output signal line of the comparator 132. A digitized heartbeat signal is output through the output signal line 133 of the comparator 132.

Figure 6:
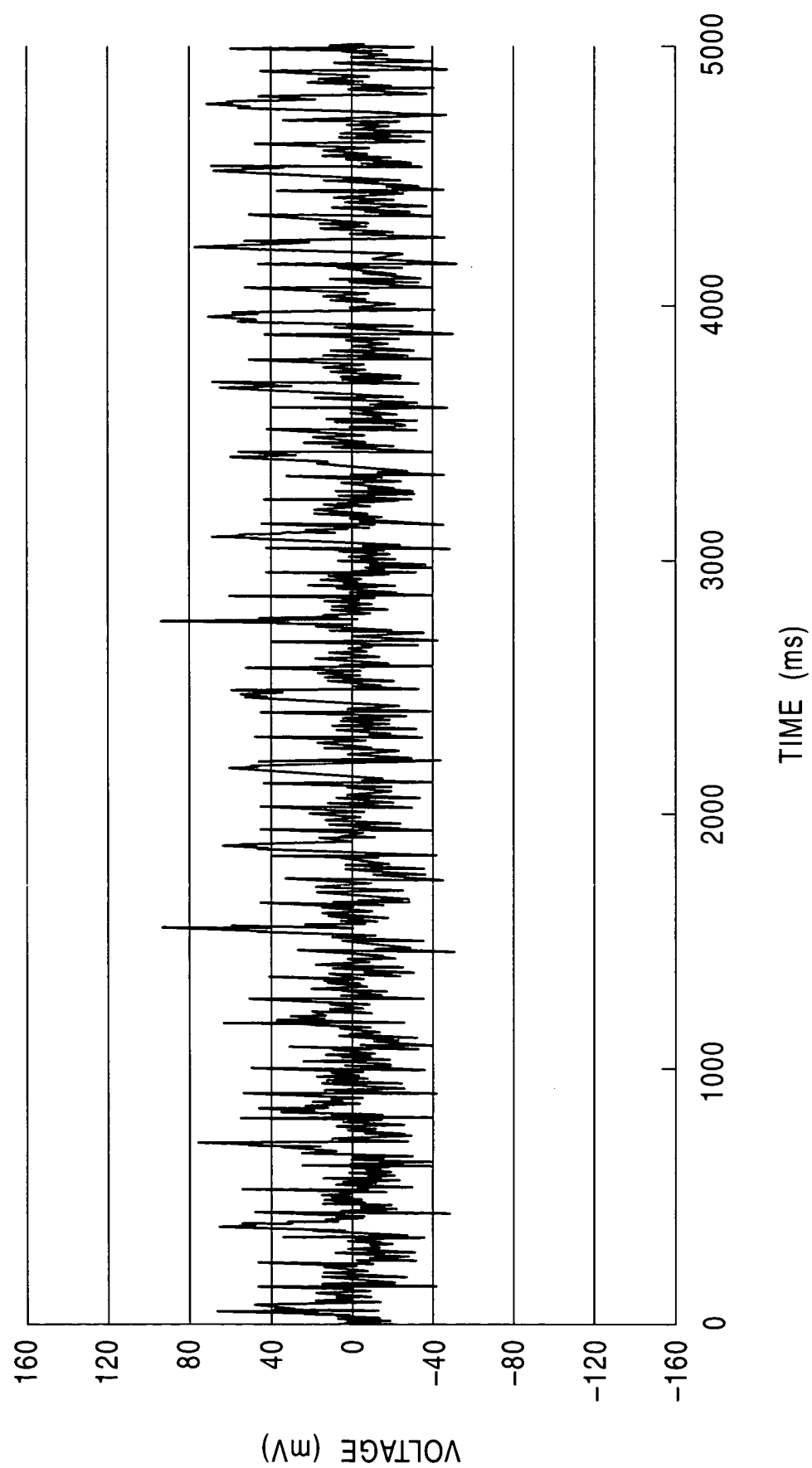
FIG. 6 is a graph showing a heartbeat signal of a mouse output from a pressure-sensitive sensor in the device for maintaining body temperature having heart rate and respiratory rate detection function for small animals according to an embodiment of the present invention, when a low-performance high-pass filter is used.
Figure 7:
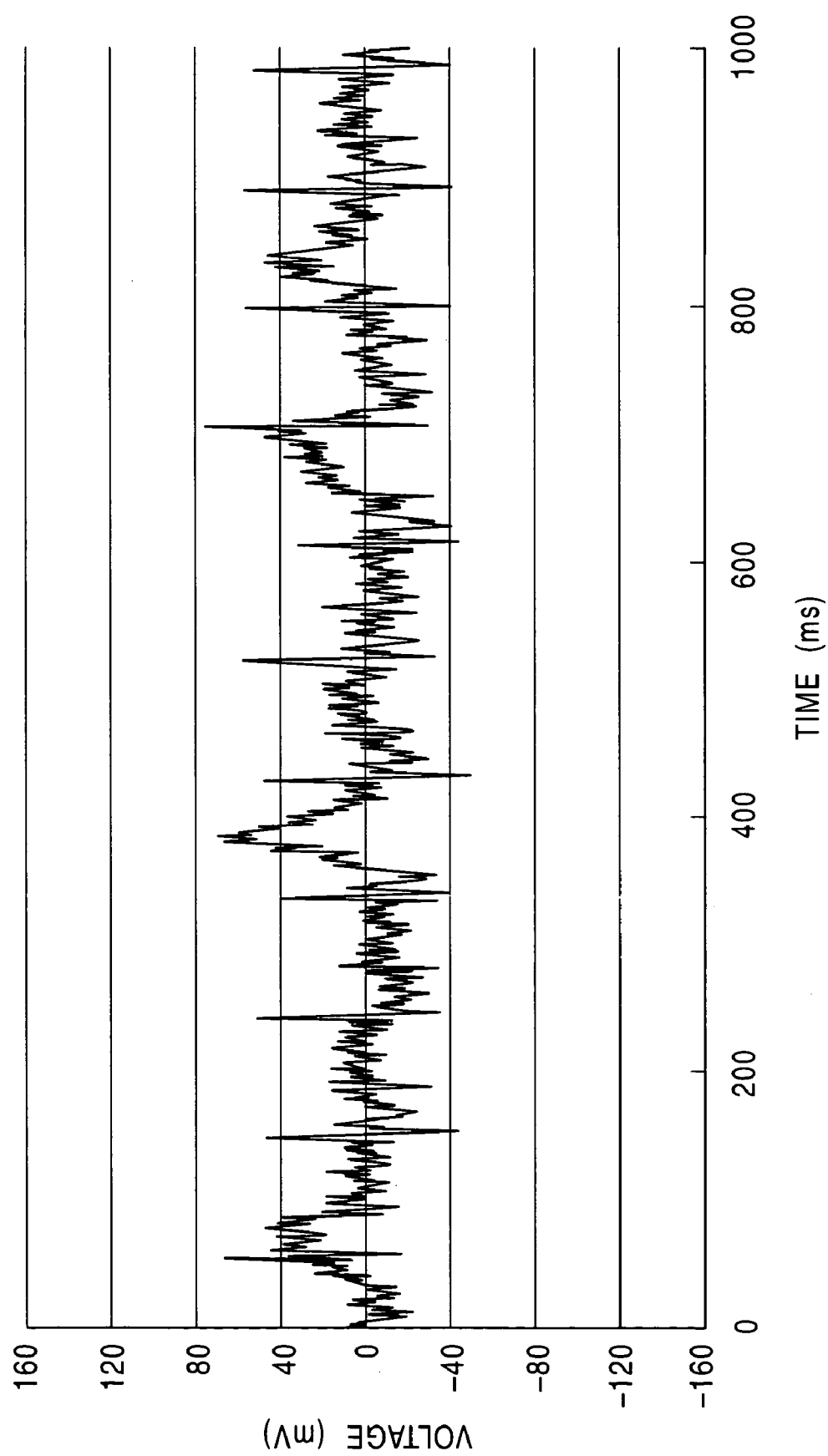
FIG. 7 is a graph showing the heartbeat signal of the mouse output from the pressure-sensitive sensor in the device for maintaining body temperature having heart rate and respiratory rate detection function for small animals when a low-performance high-pass filter is used, in which the time base in FIG. 6 is expanded.

FIG. 6 is a graph showing a heartbeat signal of a mouse output from the device for maintaining body temperature having heart rate and respiratory rate detection function for small animals, according to an embodiment of the present invention. FIG. 7 is a graph showing the heartbeat signal of the mouse output from the device for maintaining body temperature having heart rate and respiratory rate detection function for small animals, in which the time base in FIG. 6 is expanded. FIGS. 6 and 7 show the heartbeat signal of the mouse output when a low-performance high-pass filter is used. Signal components of noise and respiration are insufficiently separated in FIGS. 6 and 7.

Figure 8:
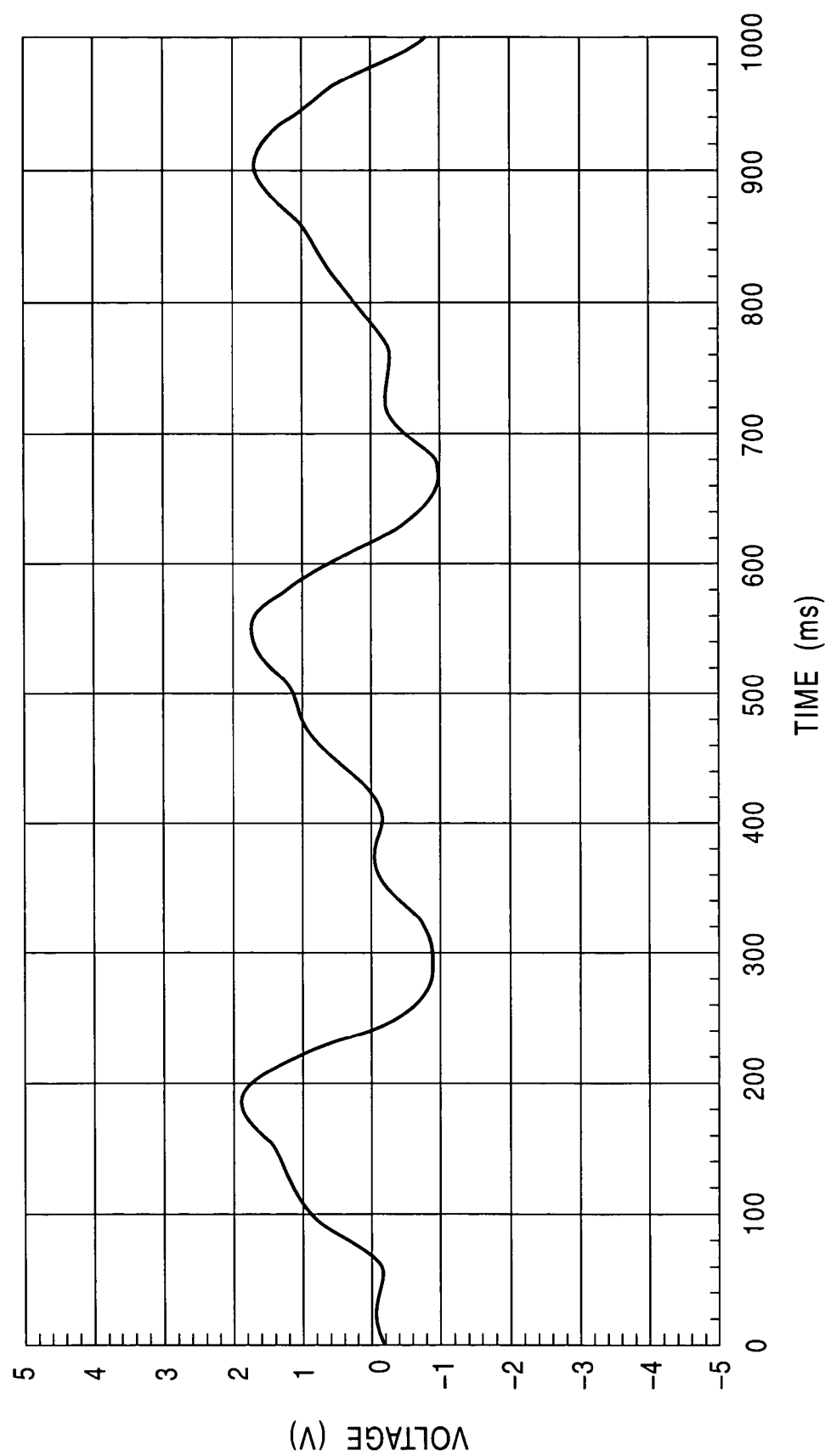
FIG. 8 is a graph showing an output from a low band-pass filter (respiration of a mouse) according to an embodiment of the present invention.

FIG. 8 is a graph showing an output from a low band-pass filter (respiration of a mouse) according to an embodiment of the present invention. A signal having a period of about 350 milliseconds representing a respiratory signal of a mouse is shown in FIG. 8. Signal components of heartbeats are completely separated.

Figure 9:
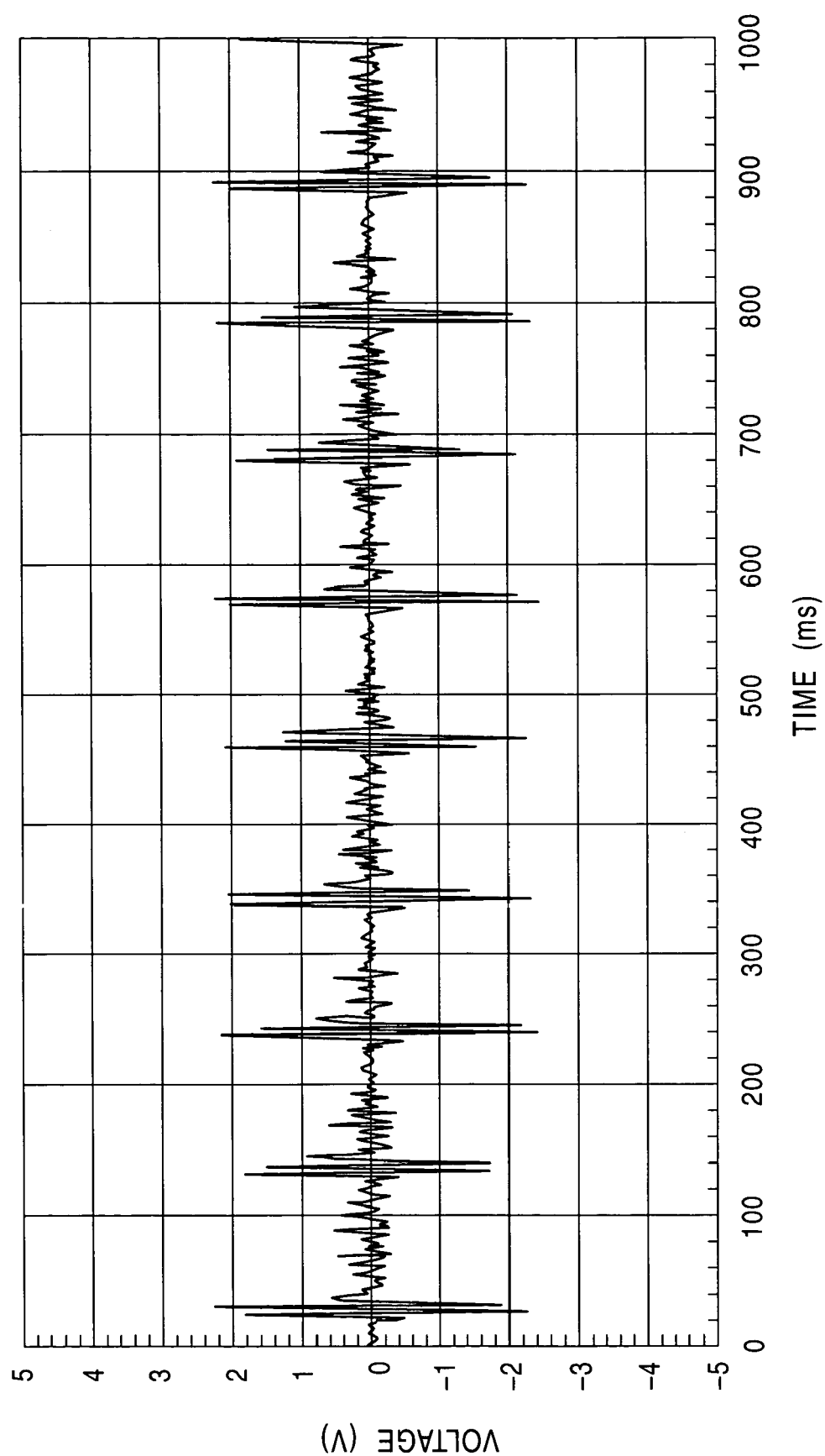
FIG. 9 is a graph (No. 1) showing an output from a high band-pass filter (heartbeats of a mouse) according to an embodiment of the present invention.

FIG. 9 is a graph showing an output from a high band-pass filter (heartbeats of a mouse) according to an embodiment of the present invention. A high-amplitude signal having a period of about 100 milliseconds representing a heartbeat signal of a mouse is shown in FIG. 9. The heartbeat signal can be visually and clearly discriminated from small noise having a low amplitude around the base line. In addition, the heartbeat signal in FIG. 9 is clearly different from the heartbeat signal shown in FIG. 7. It has been confirmed based on the correspondence to an electrocardiogram (ECG) that the signal in FIG. 9 is a heartbeat signal. As described above, with the high band-pass filter circuit of the present invention shown in FIG. 4, the analog signal output of the heartbeats of a mouse, having a high SN ratio, can be obtained.

Figure 10:
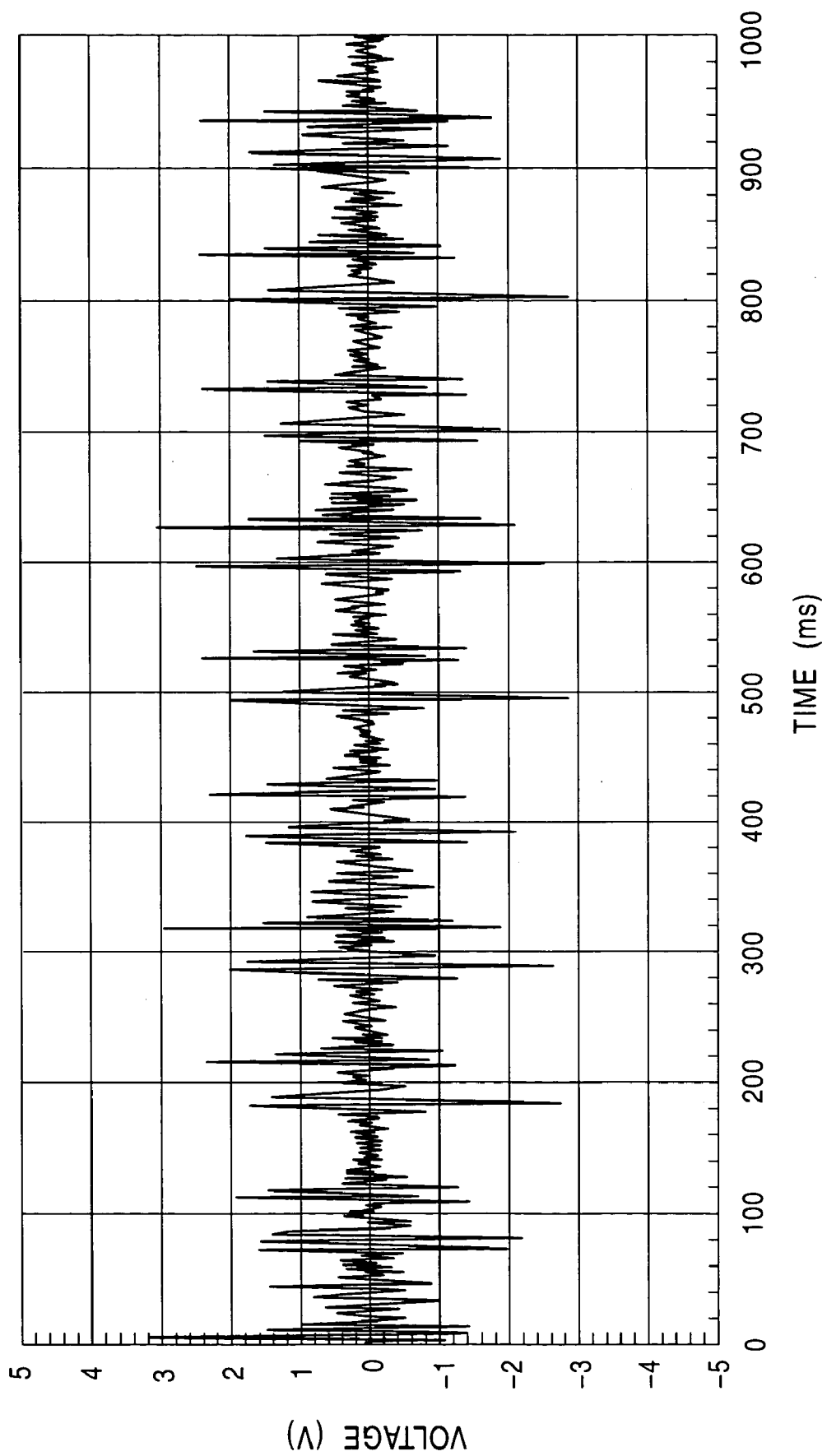
FIG. 10 a graph (No. 2) showing an output from the high band-pass filter (heartbeats of a mouse) according to the embodiment of the present invention.

FIG. 10 is a graph showing an example in which two heartbeat pulses correspond to one heartbeat, among outputs from the high band-pass filter (heartbeats of a mouse) according to an embodiment of the present invention. Referring to FIG. 10, two pulses having high amplitudes are shown during a period of about 100 milliseconds. One or two high oscillations are detected per one heartbeat with a pressure-sensitive sensor depending on the physiological state or individual difference of a small animal. Each of the oscillations is converted into one or two heartbeat pulses. An example in which two heartbeat pulses correspond to one heartbeat is shown in FIG. 10.

Referring to FIGS. 6 and 7, the horizontal axis represents time (ms) and the vertical axis represents voltage (mV). Referring to FIGS. 8 to 10, the horizontal axis represents time (ms) and the vertical axis represents voltage (V).

As described above, according to the present invention, the process for separating, shaping and displaying the electrical signal, on which the respiratory rate and the heart rate are superimposed, is performed by filtering the outputs from the pressure-sensitive sensor 4 through the low band-pass filter (LBPF) 12 and the high band-pass filter (HBPF) 13. However, since a waveform having a low SN ratio, as shown in FIGS. 6 and 7, is produced when a low-performance high-pass filter is used in the shaping of the heartbeat signals, a high-performance high band-pass filter must be used. A high band-pass filter that can be manufactured at a lower cost and that has a proprietary circuit configuration, such as the high band-pass filter circuit (HBPF) 101 shown in FIG. 4, is used in the present invention, so that an analog output waveform of the heartbeat signal having a high SN ratio, as shown in FIG. 8, can be obtained. The integration circuit 113 may be a simple series circuit including a resistor and a capacitor. The shaped signal is monitored by the external observation device 19, such as an oscilloscope. In addition, only the components highly oscillating in the positive and negative directions can be extracted within a limited time period of around several milliseconds of a heartbeat signal by using the circuit in which the positive-signal peak-hold circuit 121 and the negative-signal peak-hold circuit 125, which have a holding time of around several milliseconds, are connected to the two outputs of the differential amplifier 131 in the heartbeat-signal shaping circuit 120 within the processor 14. The addition of this circuit allows the heartbeat signal to be easily detected even when the noise level is high. The positive-signal peak-hold circuit 121 and the negative-signal peak-hold circuit 125 may be replaced with simple circuits, as shown in FIG. 5, in which the capacitors 124 and 128 are connected in parallel to the resistors 123 and 127, respectively, in the rectification circuit having the diodes 122 and 126 connected in series to the resistors. Among the output heartbeat pulses digitized in these circuits, pulses caused by noise are eliminated by a microprocessor in the processor 14, and it is determined whether a pattern is such that one pulse corresponds to one heartbeat, as shown in FIG. 9, or a pattern is such that two pulses correspond to one heartbeat, as shown in FIG. 10. The calculated result is displayed on an LED screen to monitor the respiratory rate and the heart rate of a small animal with the monitoring device 20.

As described above, according to the present invention, placing a small animal on the device for maintaining body temperature having heart rate and respiratory rate detection function for small animals allows not only the body temperature of the small animal to be maintained but also the respiratory rate and the heart rate to be monitored without being affected by noise or a change in pattern of the heartbeat signal of the small animal. This device for maintaining body temperature is a breakthrough device that has been required for eliminating the need for mounting and wiring of electrodes for an electrocardiogram and for saving time and effort for adjusting the device. The same is true for the respiratory rate measurement system for small animals, and the experimental space can be reduced because an external device is not necessary. In other words, the introduction of the device according to the present invention advantageously and largely reduces the time and effort required for preparation for an experiment and assures a sufficient experimental space. Furthermore, there is no need for additionally buying an expensive respiration monitor or electrocardiograph, thus achieving a great economical effect.

As a high-level application of the device for maintaining body temperature having heart rate and respiratory rate detection function for small animals, provision of an output interface that is used for observing the strength or pattern of the heartbeats and the lung activity of a small animal permits analysis of information indicating the physiological state of the heart, which was not capable of being measured with known methods using electrocardiogram or blood pressure, or permits analysis of the activity of the heart or lung. Hence, the present invention can attain a new development in medical research fields.

It is to be understood that the invention is not limited to the disclosed embodiments. On the contrary, the invention is intended to cover various modifications and equivalent arrangements included within the spirit and scope of the present invention.

INDUSTRIAL APPLICABILITY

With the device for maintaining body temperature having heart rate and respiratory rate detection function for small animals and the heart rate and respiratory rate measurement system for small animals using the device according to the present invention, only placing a small animal on the device for maintaining body temperature having heart rate and respiratory rate detection function for small animals allows not only the body temperature of the small animal to be maintained but also the respiratory rate and the heart rate of the small animal to be monitored. Hence, the device for maintaining body temperature having heart rate and respiratory rate detection function for small animals and the heart rate and respiratory rate measurement system for small animals using the device are preferable as experimental apparatuses for noninvasively and simply measuring physiologically-required basic data of a small animal without fail.

The invention claimed is:

1. A device for maintaining body temperature and detecting heart rate and respiratory rate of a small animal, the device having a layered structure and comprising:
   (a) a flat-plate heater;
   (b) a pressure-sensitive sensor sandwiched between thin insulation sheets superimposed on the flat-plate heater;
   (c) a planar spacer for equalizing the temperature distribution and dispersing the load of a small animal supported thereon, the spacer being sandwiched between the thin insulation sheets and having a hole in which the pressure-sensitive sensor is fitted; and
   (d) a temperature sensor provided on the spacer.

2. The device according to claim 1, wherein the spacer is a metallic plate.

3. A heart rate and respiratory rate measurement system for a small animal comprising:
   (a) a flat-plate heater;
   (b) a pressure-sensitive sensor that is sandwiched between thin insulation sheets superimposed on the flat-plate heater;
   (c) a planar spacer for equalizing the temperature distribution and dispersing the load of the small animal supported thereon, the spacer being sandwiched between the thin insulation sheets and having a hole in which the pressure sensor is fitted;
   (d) a temperature sensor provided on the spacer;
   (e) a control device for maintaining the body temperature of the small animal and for acquiring information as an electrical signal from the pressure-sensitive sensor to determine respiratory rate and heart rate, with the chest of the small animal placed over the pressure-sensitive sensor; and
   (f) a monitoring device for monitoring the respiratory rate and heart rate of the small animal.

4. The heart rate and respiratory rate measurement system according to claim 3, wherein the spacer is a metallic plate.

5. The heart rate and respiratory rate measurement system according to claim 4, further comprising a low bandpass filter for processing the information acquired from the pressure-sensitive sensor to measure the respiratory rate of the small animal and a high bandpass filter for measuring the heart rate of the small animal.

6. The heart rate and respiratory rate measurement system according to claim 5, further comprising:
   a terminal which receives outputs from the filters and which outputs analog output with waveforms of heartbeats and respiration; and
   means for converting the analog output into a digital signal to measure the heart rate and the respiratory rate.

7. The heart rate and respiratory rate measurement system according to claim 6, wherein the control device is a microprocessor including a storage medium containing a stored program for eliminating pulses caused by noise among the digitized heartbeat pulses and for determining whether the digitized heartbeat pulses are a pattern wherein one pulse corresponds to one heartbeat or a pattern wherein two pulses correspond to one heartbeat.

8. The heart rate and respiratory rate measurement system according to claim 6, further comprising a high band-pass filter circuit comprising:
   a high-pass filter for producing a filtered output;
   an amplifier for amplifying the filtered output to produce an amplified signal; and
   an integration circuit that receives the amplified signal with output to a first differential amplifier which supplies the analog output.

9. The heart rate and respiratory rate measurement system according to claim 8, the means for converting the analog output into the digital signal is a circuit comprising:
   a positive-signal peak-hold circuit and a negative-signal peak-hold circuit, both of which have a holding time of around several milliseconds and are connected to two input terminals of a second differential amplifier.

10. The heart rate and respiratory rate measurement system according to claim 9, wherein each of the peak-hold circuits includes a capacitor connected in parallel to a resistor in a rectification circuit having a diode connected in series to the resistor.

11. The heart rate and respiratory rate measurement system according to claim 5, further comprising:
   a terminal which receives outputs from the filters and which outputs analog output with waveforms of heartbeats and respiration
   display device for observing the heartbeats and the respiration based on the output from the terminal.

* * * * *

UNITED STATES PATENT AND TRADEMARK OFFICE
CERTIFICATE OF CORRECTION

PATENT NO.        : 7,174,854 B2                                    Page 1 of 1
APPLICATION NO. : 10/503985
DATED             : February 13, 2007
INVENTOR(S)       : Shinichi Sato et al.

It is certified that error appears in the above-identified patent and that said Letters Patent is hereby corrected as shown below:

On The Title Page, Item -57-
IN THE ABSTRACT
   Line 1, change "temperature with" to read -- temperature, with --; and
   Line 2, change "rate small" to read -- rate, of small --.

Column 10, line 12 (claim 11, line 5) after "respiration" insert -- ; and --; and
Column 10, line 13 (claim 11, line 6) "display" should read -- a display --.

Signed and Sealed this

Twenty-sixth Day of June, 2007

JON W. DUDAS
*Director of the United States Patent and Trademark Office*